(12) United States Patent
Rollat et al.

(10) Patent No.: US 6,517,821 B1
(45) Date of Patent: Feb. 11, 2003

(54) RESHAPABLE HAIR STYLING COMPOSITION COMPRISING AQUEOUS COLLOIDAL DISPERSIONS OF SULFONATED POLYURETHANE UREA

(75) Inventors: Isabelle Rollat, Paris (FR); Henri Samain, Bièvres (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/627,121

(22) Filed: Jul. 27, 2000

(51) Int. Cl.$^7$ .............................. A61K 7/00; A61K 7/06
(52) U.S. Cl. ..................... 424/70.11; 424/70.1; 424/45; 424/47
(58) Field of Search ................................ 424/401, 70.1, 424/70.11, 47, 45

(56) References Cited

U.S. PATENT DOCUMENTS

| | | |
|---|---|---|
| 2,958,593 A | 11/1960 | Hoover et al. |
| 2,988,538 A | 6/1961 | Thoma et al. |
| 3,708,333 A | 1/1973 | Carlson |
| 3,826,769 A | 7/1974 | Carlson |
| 3,941,733 A | 3/1976 | Chang |
| 3,971,745 A | 7/1976 | Carlson et al. |
| 3,993,614 A | 11/1976 | Carlson |
| 3,998,870 A | 12/1976 | Carlson |
| 3,998,871 A | 12/1976 | Carlson |
| 4,108,814 A | 8/1978 | Reiff et al. |
| 4,110,284 A | 8/1978 | Violland et al. |
| 4,150,946 A | 4/1979 | Neel et al. |
| 4,224,418 A | 9/1980 | Dieterich et al. |
| 4,227,350 A | 10/1980 | Fitzer |
| 4,300,580 A | * 11/1981 | O'Neil et al. |
| 4,307,219 A | 12/1981 | Larson |
| 4,501,852 A | 2/1985 | Markusch et al. |
| 4,539,366 A | 9/1985 | Gagne et al. |
| 4,558,149 A | 12/1985 | Larson |
| 4,569,982 A | 2/1986 | Groggler et al. |
| 4,638,017 A | 1/1987 | Larson et al. |
| 4,652,466 A | 3/1987 | Thoma et al. |
| 4,696,760 A | 9/1987 | Morimoto et al. |
| 4,738,992 A | 4/1988 | Larson et al. |
| 4,746,717 A | 5/1988 | Larson |
| 4,774,937 A | 10/1988 | Scholz et al. |
| 4,780,523 A | 10/1988 | Chung |

(List continued on next page.)

FOREIGN PATENT DOCUMENTS

| | | |
|---|---|---|
| EP | 0 039 162 | 11/1981 |
| EP | 0 524 346 | 1/1993 |
| EP | 0 598 312 | 5/1994 |
| EP | 0 637 600 | 2/1995 |
| EP | 0 656 021 | 6/1995 |
| EP | 0 696 607 | 2/1996 |
| EP | 0 705 093 B1 * | 4/1996 |
| EP | 0 779 310 | 6/1997 |
| EP | 0 794 203 | 9/1997 |
| EP | 0 937 451 | 8/1999 |
| EP | 0 938 889 | 9/1999 |
| EP | 0 957 119 | 11/1999 |
| EP | 0 966 946 | 12/1999 |
| EP | 1 068 859 | 1/2001 |
| JP | 10-203937 | 8/1998 |
| WO | WO 94/03510 | 2/1994 |
| WO | WO 95/08583 | 3/1995 |
| WO | WO 97/03252 | 1/1997 |
| WO | WO 97/17052 | 5/1997 |
| WO | WO 97/17386 | 5/1997 |
| WO | WO 98/38969 | 9/1998 |
| WO | 98/38969 * | 9/1998 |
| WO | WO 99/05192 | 2/1999 |
| WO | WO 99/58100 | 11/1999 |

OTHER PUBLICATIONS

Derwent Abstract of EP 0 637 600.
Derwent Abstract of EP 0 938 889.
Derwent Abstract of EP 0 957 119.
Derwent Abstract of EP 0 966 946.
Derwent Abstract of JP 10–203937.
English language translation of JP 10–203937.
Dialog Abstract of JP 10–203937.
U.S. patent application Ser. No. 09/380,467, Hairstyling Composition Capable Of Being Remodelled, Isabelle Rollat et al., Filed Sep. 3, 1999.
U.S. patent application Ser. No. 09/627,055, Reshapable Hair Styling Composition Comprising Acrylic Emulsions Isabelle Rollat et al. Filed Jul. 27, 2000.
U.S. patent application Ser. No. 09/695,092; Reshapable Hair Styling Compositions Comprising Acrylic Emulsions, Isabelle Rollat et al., filed Oct. 25,2000.
U.S. patent application Ser. No. 09/627,585; Reshapable Hair Styling Composition Comprising Polyurethane Dispersions, Isabelle Rollat et al., filed Jul. 27, 2000.
U.S. patent application Ser. No. 09/769,311; Reshapable Hair Styling Composition Comprising Silicon–Containing Polycondensates, filed Isabelle Rollat et al., Jan. 26, 2001.
U.S. patent application Ser. No. 09/866,013; Reshapable Hair Styling Composition Comprising Heterogeneous (Meth)Acrylic Copolymer Particles, Isabelle Rollat et al., filed Jun. 22, 2001.
U.S. application patent Ser. No. 09/866,009; Reshapable Hair Styling Composition Comprising (METH)Acrylic Copolymers of Four or More Monomers, Isabelle Rollat et al., filed Jun. 22, 2001.

Primary Examiner—Thurman K. Page
Assistant Examiner—S. Howard
(74) Attorney, Agent, or Firm—Finnegan, Henderson, Farabow, Garrett & Dunner, LLP

(57) ABSTRACT

A reshapable hair styling composition comprising, in a cosmetic vehicle appropriate for hair, at least one sulfonated polyurethane urea obtained by reacting: (a) at least one sulfonated polyol, (b) at least one non-sulfonated polyol, (c) at least one polyisocyanate selected from aliphatic and cycloaliphatic polyisocyanates, and (d) excess water, wherein the sulfonated polyurethane urea has been chain-extended.

36 Claims, No Drawings

U.S. PATENT DOCUMENTS

| | | |
|---|---|---|
| 4,855,384 A | 8/1989 | Larson |
| 4,856,502 A | 8/1989 | Ersfeld et al. |
| 4,922,675 A | 5/1990 | Sato et al. |
| 4,937,283 A | 6/1990 | Chung |
| 5,039,733 A | 8/1991 | Dormish et al. |
| 5,071,578 A | 12/1991 | Ohkubo et al. |
| 5,085,941 A | 2/1992 | Ohkubo et al. |
| 5,110,843 A | 5/1992 | Bries et al. |
| 5,118,850 A | 6/1992 | Bowman et al. |
| 5,134,035 A | 7/1992 | Kumar et al. |
| 5,203,884 A | 4/1993 | Buchanan et al. |
| 5,218,072 A | 6/1993 | Kumar et al. |
| 5,240,972 A | 8/1993 | Kumar et al. |
| 5,244,739 A | 9/1993 | Carlson et al. |
| 5,260,136 A | 11/1993 | Ohkubo et al. |
| 5,334,690 A | 8/1994 | Schafheutle et al. |
| 5,344,873 A | 9/1994 | Blum |
| 5,367,017 A | 11/1994 | Rosrhauser et al. |
| 5,370,910 A | 12/1994 | Hille et al. |
| 5,427,835 A | 6/1995 | Morrison et al. |
| 5,468,498 A | * 11/1995 | Morrison et al. |
| 5,531,039 A | 7/1996 | Gore |
| 5,609,969 A | 3/1997 | Claranoff et al. |
| 5,610,232 A | 3/1997 | Duan et al. |
| 5,626,840 A | 5/1997 | Thomaides et al. |
| 5,637,639 A | 6/1997 | Duan et al. |
| 4,049,396 A | 7/1997 | Hiles |
| 5,650,159 A | 7/1997 | Lion et al. |
| 5,660,816 A | 8/1997 | Adams et al. |
| 5,674,479 A | 10/1997 | George et al. |
| 5,679,754 A | 10/1997 | Larson et al. |
| 5,703,158 A | 12/1997 | Duan et al. |
| 5,846,524 A | 12/1998 | Breitenbach et al. |
| 5,853,701 A | * 12/1998 | George et al. |
| 5,972,354 A | 10/1999 | de la Poterie et al. |
| 6,007,794 A | * 12/1999 | George et al. |
| 6,132,704 A | * 10/2000 | Bhatt et al. |
| 6,136,884 A | * 10/2000 | Chen et al. |
| 6,165,239 A | * 12/2000 | Hedrick et al. |

\* cited by examiner

RESHAPABLE HAIR STYLING COMPOSITION COMPRISING AQUEOUS COLLOIDAL DISPERSIONS OF SULFONATED POLYURETHANE UREA

The present invention relates to a reshapable hair styling composition.

Fixing the hairstyle is an important element in hair styling, and involves maintaining a shaping that has already been carried out, or in simultaneously shaping and fixing the hair.

In accordance with the invention, the term "hair styling composition" relates to any kind of hair composition that can be used to effect hair styling, for example fixing compositions, shampoos, conditioners, permanent waving compositions, hair care products, and hair treatment products.

The most prevalent hair styling compositions on the cosmetic market for shaping and/or maintaining the hairstyle are spray compositions comprising a solution, usually alcohol- or water-based, and one or more materials, generally polymer resins. One of the functions of polymer resins is to form links between the hairs, these materials also being called fixatives, in a mixture with various cosmetic adjuvants. This solution is generally packaged either in an appropriate aerosol container, which is pressurized with the aid of a propellant, or in a pump flask.

Other known hair styling compositions include styling gels and mousses, which are generally applied to the wetted hair before brushing or setting it. In contrast to the conventional aerosol lacquers, these compositions have the disadvantage that they do not allow the hair to be fixed in a shape created before their application. In fact, these compositions are essentially aqueous and their application wets the hair and is therefore unable to maintain the initial shape of the hairstyle. In order to shape and fix the hairstyle, therefore, it is necessary to carry out subsequent brushing and/or drying.

Such hair styling compositions all have the same disadvantage that they do not allow the hairstyle to be later modified to a desired shape, which is other than that formed initially, without starting the styling and fixing operations again. Moreover, under various kinds of stress, the hairstyle has a tendency to take on an undesirable permanent set, which cannot easily be modified. Also in the styling process, one desires hair conditioning benefits, such as ease of combing and soft hair feel appearance.

A subject of the invention is a reshapable hair styling composition comprising, in a cosmetic vehicle appropriate for hair, at least one polyurethane urea comprising a residue of at least one sulfonated polyol.

Another subject of the invention is a reshapable hair styling composition comprising, in a cosmetic vehicle appropriate for hair, at least one dispersion comprising at least one polyurethane urea comprising a residue of at least one sulfonated polyol.

Another subject of the invention is a reshapable hair styling composition comprising, in a cosmetic vehicle appropriate for hair, at least one colloidal dispersion comprising at least one polyurethane urea comprising a residue of at least one sulfonated polyol.

Another subject of the invention is a reshapable hair styling composition comprising, in a cosmetic vehicle appropriate for hair, at least one dispersion comprising at least one sulfonated polyurethane urea being obtained by reacting:

(a) at least one sulfonated polyol;
(b) at least one non-sulfonated polyol;
(c) at least one polyisocyanate chosen from aliphatic polyisocyanates, having 1 to 25 carbon atoms, and cycloaliphatic polyisocyanates, having 3 to 25 carbon atoms; and
(d) excess water, wherein:
    the sulfonated polyurethane urea has been chain-extended.

Another subject of the invention is a reshapable hair styling composition comprising, in a cosmetic vehicle appropriate for hair, at least one dispersion comprising at least one sulfonated polyurethane urea being obtained by reacting:

(a) at least one sulfonated polyol;
(b) at least one non-sulfonated polyol;
(c) at least one polyisocyanate chosen from aliphatic polyisocyanates, having 1 to 25 carbon atoms, and cycloaliphatic polyisocyanates, having 3 to 25 carbon atoms; and
(d) excess water, wherein:
    the sulfonated polyurethane urea has been chain-extended with water;
    the reaction product of (a), (b), and (c) has an isocyanate to hydroxyl ratio ranging from about 1.3:1 to about 2.5:1; and
    the reaction product of (a), (b), and (c) with (d) has a sulfonate equivalent weight of from about 1000 to about 8500 and comprises a polyurea segment of the following formula:

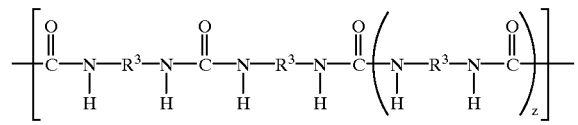

wherein z is an integer from 0 to 6; and $R^3$ is chosen from aliphatic groups, having 1 to 25 carbon atoms, and cycloaliphatic groups, having 3 to 25 carbon atoms, derived from aliphatic and cycloaliphatic polyisocyanates.

Another subject of the invention is a reshapable hair styling composition comprising, in a cosmetic vehicle appropriate for hair, the above described dispersion comprising at least one sulfonated polyurethane urea, wherein the dispersion is a colloidal dispersion.

The term "reshapable" hair styling composition means a hair styling composition providing hair styling that can be restored or modified without new material or heat being applied. For example, in order to restore or modify the hairstyle in case of "drooping" or loss of setting (dishevelment), no new materials, such as water or any form of fixing agent, or heat are required. Thus, to provide a "reshapable" effect means to provide a hair styling that can be restored or modified without new material or heat being applied. The efficacy of the composition can be long lasting, such as 10–24 hours, giving rise to a durable styling effect. Other terms, which may be synonymous with reshapable, include repositionable, remoldable, restyleable, and remodellable.

"Aliphatic" means a non-aromatic group, which can be a straight or branched chain alkylene group of 1 to 25 carbon atoms wherein these groups may be optionally substituted, for example with a group chosen from ether, ester, and cycloaliphatic functional groups.

"Colloidal dispersion" means a discrete distribution of particles having an average size of less than about 1 micron, typically less than about 500 nanometers, in an aqueous media (water).

"Cycloaliphatic" means a non-aromatic, optionally substituted cyclic group of 3 to 25 carbons, wherein one to three carbon atoms each may be optionally replaced with a heteroatom, for example nitrogen or oxygen, or C(O). The cycloaliphatic group may be optionally substituted, for example with a group chosen from alkyl, ether, and ester functional groups.

"Polyurea" means a polymer obtained by a polymerization reaction in which the mechanism for chain growth is entirely the formation of urea and biuret linkages by the reaction of isocyanate groups with amine or urea groups, with urea linkage formation predominating.

"Stable aqueous colloidal dispersion" means a discrete distribution of particles having an average size of less than about 1 micron, typically less than about 500 nanometers, in an aqueous media (water) that do not agglomerate in the absence of agitation (either continuous or intermittent).

"Sulfonate equivalent weight" means the sum of the atomic weights of all of the atoms in the sulfopolyurea divided by the number of sulfonate groups contained in the polymer molecule.

"Sulfopolyurea" means a high molecular weight polyurea containing a plurality of sulfonate groups covalently bonded to and pendant from the polymer chain.

"Sulfonated polyurethane urea" refers to a polymer containing sulfonate groups and a plurality of urea linkages and urethane linkages.

In one embodiment of the invention, the sulfonated polyurethane ureas of the present invention are obtained by reacting: (a) at least one sulfonated polyol, (b) at least one non-sulfonated polyol, (c) at least one polyisocyanate chosen from aliphatic and cycloaliphatic polyisocyanates, and (d) excess water, wherein the reaction product of (a), (b), and (c) with (d) comprises a polyurea segment of the following formula:

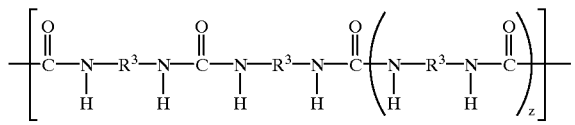

wherein z is an integer from 0 to 6; and $R^3$ is chosen from aliphatic groups, having 1 to 25 carbon atoms, and cycloaliphatic groups, having 3 to 25 carbon atoms, derived from the aliphatic and cycloaliphatic polyisocyanates. The reaction of (a), (b), and (c) forms an isocyanate terminated prepolymer mixture that has an isocyanate to hydroxyl ratio of about 1.3:1 to about 2.5:1. The reaction product of (a), (b), and (c) with (d) provides a sulfonated polyurethane urea that has a sulfonate equivalent weight of from about 1000 to about 8500 and that has been chain-extended with water.

The term "polyol" as used herein refers to polyhydric alcohols comprising two or more hydroxyl groups. The polyols can be hydrophilic or hydrophobic. The term "polyol" as used herein includes non-sulfonated polyols and sulfonated polyols. A non-sulfonated polyol is a polyol that does not contain a sulfonate group pendant from the polyol backbone. A sulfonated polyol is a polyol that contains at least one sulfonate group ($SO_3M$ wherein M is a cation chosen from alkali metal cations $Na^+$, $Li^+$, and $K^+$) pendant from the polyol backbone. Sulfonated polyols can be made from non-sulfonated polyols by a transesterification or an esterification reaction.

One class of polyols suitable for use in the present invention includes polyols having molecular weights in the range of from about 200 to about 2000. The polyols may comprise divalent aliphatic and/or cycloaliphatic groups comprising ether and/or ester functional groups.

Polyols suitable for use in the present invention can be chosen from polyether polyols, polyester polyols, polycaprolactone polyols, and the like, and mixtures thereof. Polyols of the present invention are typically diols, including, but not limited to, 400 average molecular weight polyethylene glycol (available from DuPont Chemicals, Wilmington, Del.), 600 average molecular weight polyethylene glycol (available from Union Carbide Chemical and Plastics Co., Inc., Danbury, Conn.), 300 average molecular weight polyethylene glycol (available from Aldrich Chemical Co., Milwaukee, Wis.), 425 average molecular weight polypropylene glycol (available from Arco Chemical, Newton Square, Pa.), and polycaprolactonediol (PCP-200, available from Union Carbide Corp.). Also, mixtures of polyols can be used. One embodiment of a suitable polyol is a mixture of polyethylene glycol with a hydroxy equivalent weight of 200 and polypropylene glycol with a hydroxy equivalent weight of 212. Other polyols useful in the present invention include polycaprolactone polyols and polytetramethylene glycols. Additionally, polyester diols made from diesters or diacids and diols may be utilized. Diesters useful for making polyester diols include dimethyl isophthalate, dimethyl terephthalate, dimethyl adipate, and the like. Diols useful for making polyester diols include propylene glycol, 1,3-propane diol, 1,4-butane diol, and the like.

In one embodiment, sulfonated polyols are prepared under typical transesterification or esterification reaction conditions, using one or more of the polyols indicated above, other diols, or combinations of the polyols and other diols with dimethyl-5-sodiosulfoisophthalate (DMSSIP CAS# 3965-55-7, commercially available from Aldrich Chemical Company, Milwaukee, Wis.) or 5-sodiosulfoisophthalic acid (SSIP CAS# 6362-79-4, commercially available from Aldrich Chemical Company, Milwaukee, Wis.), and a transesterification reaction catalyst (for example, tetrabutyl titanate, commercially available from Aldrich Chemical Company, Milwaukee, Wis.). Typically an excess of the polyol (up to as much as a 4:1 molar excess polyol relative to dimethyl-5-sodiosulfoisophthalate) is used in the formation of the sulfonated polyol. When the reaction is complete, the product is a mixture of sulfonated polyols and non-sulfonated polyols.

Polyisocyanates used in the preparation of the sulfonated polyurethane ureas of the present invention are aliphatic polyisocyanates, cycloaliphatic polyisocyanates, and mixtures thereof. A wide variety of aliphatic and cycloaliphatic polyisocyanates may be utilized. Polyisocyanates of the present invention are any aliphatic and/or cycloaliphatic organic compounds that have two or more reactive isocyanate (i.e., —NCO) groups in a single molecule. This definition encompasses diisocyanates, triisocyanates, tetraisocyanates, etc., and mixtures thereof. A particularly well-known and useful class of polyisocyanates are diisocyanates.

Suitable polyisocyanates include, but are not limited to, isophorone diisocyanate, (IPDI), commercially available from Bayer Corp., Pittsburgh, Pa. as Desmodur I™, bis(4-isocyanatocyclohexyl)methane ($H_{12}MDI$), commercially available from Bayer Corp. as Desmodur W™, trimethyl-1,6-diisocyanatohexane (TMDI, CAS # 34992-02-4), 1,6-hexane diisocyanate (HDI, available from Aldrich Chemical Co., Milwaukee, Wis. (CAS # 822-06-0)), and mixtures thereof.

Excess water means that the water is present in an amount greater than the amount of isocyanate terminated prepolymer mixture (w/w) such that a final aqueous dispersion of less than 50% solids is achieved. Water may be also used to chain extend the prepolymer mixture.

In the sulfonated polyurethane urea of the present invention, at least one sulfonate group ($SO_3M$) is pendant from the sulfonated polyurethane urea backbone. The term pendant as used herein refers to a moiety bonded to an interior portion of the sulfonated polyurethane urea. Representative sulfonated polyurethane ureas may have a sulfonate group equivalent weight of from about 1000 to about 8500, such as from about 3000 to about 6000. M designates a cation chosen from alkali metal cations $Na^+$, $Li^+$, and $K^+$.

In one embodiment, the $SO_3M$ group is an aromatic sulfonate group (i.e., pendant from an aromatic moiety incorporated into the sulfonated polyurethane urea), wherein M is $Na^+$. At least one example of this type of compound is readily available from commercial sources, including, for example, DuPont. Therefore, it can be easily incorporated into the sulfonated polyurethane urea, and its properties are well known.

An example of the aromatic sodium sulfonate compound is dimethyl-5-sodiosulfoisophthalte (DMSSIP).

The sulfonated polyurethane urea polymer backbone is a polymer that contains a plurality of urethane segments and a plurality of urea segments. The urethane segments are derived from the reaction of sulfonated polyols, non-sulfonated polyols, and aliphatic and/or cycloaliphatic polyisocyanates to form an isocyanate terminated prepolymer mixture. The urea segments of the polymer are derived from the reaction of the isocyanate terminated prepolymer mixture with water.

The amount of urea segments to urethane segments arises from the isocyanate (—NCO) to polyol (—OH) ratio of the isocyanate terminated prepolymer, a higher ratio indicating more free isocyanate. Therefore, this isocyanate to hydroxyl ratio (NCO/OH) of the isocyanate terminated prepolymer mixture ultimately determines the molecular weight and physical properties of the sulfonated polyurethane urea generated. In one embodiment of the invention, a NCO/OH ratio of about 1.3:1 to about 2.2:1, also from it) about 1.65:1 to about 1.85:1, and further also about 1.75:1, is used to generate an isocyanate terminated prepolymer with an average molecular weight of about 700 to about 2500, such as from about 1200 to about 1700. If the average molecular weight of the isocyanate terminated prepolymer mixture is too high, the prepolymer mixture becomes too viscous.

A representative NCO/OH ratio is about 1.3:1 to about 2.2:1. When the NCO/OH ratio is of about 1.65:1 to about 1.85:1, such as about 1.75:1, the amount of urea segments to urethane segments in the sulfonated polyurethane urea is even more evenly balanced.

One exemplary preparation of the sulfonated polyurethane ureas used in the compositions according to the invention is schematically depicted in the following Scheme A:

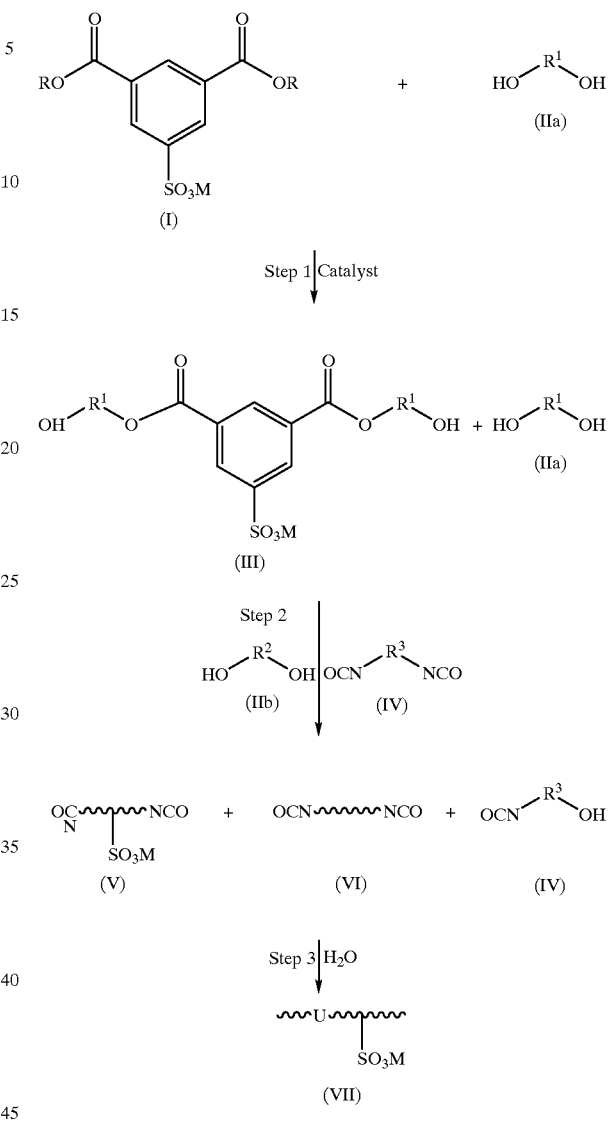

SCHEME A

In Step 1 of Scheme A, a transesterification or esterification reaction is performed in which a compound of formula (I) is reacted with a polyol (IIa) in the presence of a catalyst. Each R is identical or different and chosen from a hydrogen atom and a methyl group. $R^1$ is a divalent group chosen from aliphatic groups and cycloaliphatic groups having an average molecular weight of about 200 to about 2,000 comprising at least one group chosen from ether and ester functional groups. This reaction yields a sulfonated polyol (III) and unreacted/excess polyol (IIa). Suitable catalysts include, for example, tetrabutyl titanate (TBT), zinc chloride, sodium alkoxides, cadmium acetate, and lead acetate. The transesterification or esterification reaction is performed at approximately 170° C. Polyol (IIa) may be a single polyol or a mixture of polyols, producing a single sulfonated polyol (III) or a mixture of sulfonated polyols (III).

In Step 2, sulfonated polyol (III) and polyol (IIa) are reacted with polyisocyanate (IV), and optionally polyol (IIb). $R^3$ is chosen from aliphatic groups, having 1 to 25 carbon atoms, and cycloaliphatic groups, having 3 to 25 carbon atoms, derived from the aliphatic and cycloaliphatic polyisocyanates. $R^2$ is a divalent group chosen from aliphatic groups and cycloaliphatic groups having an average molecular weight of about 200 to about 2,000 comprising at least one group chosen from ether and ester functional groups. This reaction provides isocyanate terminated prepolymer (V) and (VI) and unreacted/excess polyisocyanate (IV). In this Step, polyol (IIb) may be the same or different than polyol (IIa). Both polyol (IIa) and polyol (IIb) may be a single polyol or a mixture of polyols and polyisocyanate (IV) may be a single polyisocyanate or a mixture of polyisocyanates. The isocyanate terminated prepolymers (V) and (VI) are obtained by reacting polyisocyanate (IV) with at least one of the polyols chosen from sulfonated polyol (III), polyol (IIa), and polyol (IIb). Therefore, the end-product of Step 2 comprises an isocyanate terminated prepolymer mixture including isocyanate terminated sulfonated prepolymer (V), isocyanate terminated prepolymer (VI), and excess polyisocyanate (IV). The isocyanate terminated sulfonated prepolymer (V) produced by the above described process are described in U.S. Pat. Nos. 4,558,149, 4,746,717, and 4,855,384, which are incorporated herein by reference in their entirety.

In Step 3, the isocyanate terminated prepolymer mixture, [(V), (VI), and (IV)], is mixed, with sufficient agitation to avoid macroscopic gel formulation, with excess water preheated to approximately 50–65° C. This addition produces an aqueous colloidal dispersion of sulfonated polyurethane ureas (VII). Excess water means that the amount of water is greater than the amount of isocyanate terminated prepolymer mixture. The sulfonated polyurethane urea (VII) comprises at least one U, which is a polyurea segment of the following formula:

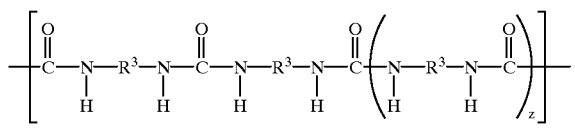

wherein $R^3$ is derived from the polyisocyanate (IV) and is as defined previously and z is an integer from 0 to 6. The reaction may be stirred at approximately 95° C. for 1–3 hours. Mixing methods may be employed that provide adequate levels of shear or agitation to avoid formation of macroscopic gel particles.

Chain extension can be accomplished with water. In another embodiment, chain extension may be accomplished with a diamine ($H_2N$~~~$NH_2$). Co-solvents, such as volatile organic compounds, are not necessary. Therefore, in at least certain embodiments of the invention, exposure to and disposal of potentially harmful volatile organic chemicals has been eliminated.

Subsequent to being introduced into the aqueous environment in step 3, a portion of the isocyanate groups react with water to form amino groups and $CO_2$. These amino groups spontaneously react with another isocyanate group to form urea linkages in the sulfonated polyurethane ureas.

This process produces a discreet aqueous distribution or aqueous dispersion of sulfonated polyurethane urea particles less than one micron in diameter, typically ranging from about 10 nanometers to about 500 nanometers in diameter. The dispersions can have a translucent, bluish appearance characteristic of a colloidal dispersion or can range from a clear light yellow solution to a milky white dispersion.

The medium of dispersion is a water and/or solvent medium of dispersion. In one embodiment, the dispersing medium may be chosen from lower alcohols ($C_1$ to $C_4$ branched or straight chain aliphatic alcohols), water, and mixtures thereof. The lower alcohols may be chosen from ethanol, n-propanol, and 2-propanol (IPA). Alternatively, the medium may be chosen from water, IPA, ethanol, and mixtures thereof. The alcohol to water ratio may range from 20:80 to 90:10 w/w and also from 70:30 to 85:15. In general, higher amounts of alcohol will result in a dispersion that exhibits faster dry times.

The solvent system may comprise other solvents. For example, other rapid evaporating, skin compatible solvents may be used, such as hexamethyldisiloxane (HMDS); cyclic silicones ($D_4$ and $D_5$); $C_4$–$C_{10}$ alkanes including isoparafins such as Permethyl 97A and Isopar C; acetone; hydrofluoroethers (HFEs) and the like. Certain HFEs, such as HFE 7100, have an added benefit in certain applications; when such a solvent is added to hydro-alcohol mixtures in levels above about 15 to about 25 wt %, the composition becomes non-flammable.

An embodiment of the invention provides a reshapable hair styling composition comprising, in a cosmetic vehicle suitable for hair, at least one dispersion comprising at least one polyurethane urea, leading to a styling material following application to the fibers and drying.

It is a further subject of the invention to provide a method for treating hair, characterized in that the composition according to the invention is applied to the hair before, during, or after the shaping of the hairstyle.

In another embodiment of the invention, the polyurethane urea has a glass transition temperature (Tg) ranging from about −100 to about 15° C. According to the present invention, the Tg of the polyurethane urea is obtained following the application of the polyurethane dispersion to a substrate and drying. The glass transition temperature is determined by the Differential Scanning Calorimetric method (DSC).

The composition according to the invention may comprise at least one other constituent, which is conventional in cosmetics, chosen from preservatives; perfumes; UV filters; active haircare agents; plasticizers; anionic, cationic, amphoteric, nonionic, and zwitterionic surfactants; hair conditioning agents such as silicone fluids, fatty esters, fatty alcohol, long chain hydrocarbons, emollients, lubricants, and penetrants such as lanolin compounds, protein hydrolysates, and other protein derivatives; anionic, cationic, amphoteric, nonionic, and zwitterionic polymers; dyes; tints; bleaches; reducing agents; pH adjusting agents; sunscreens; preservatives; thickening agents; and perfumes.

The appropriate cosmetically acceptable vehicle is adapted to the method of application selected. The vehicle preferably comprises an appropriate solvent to which may be added additives such as gelling agents, foaming agents, and silicones.

It is understood that the person skilled in the art will know how to choose the additional constituents and their amount in the composition according to the invention, such as the constituents of the vehicle, so as not to adversely affect or substantially affect its reshapable hair styling properties.

The compositions according to the invention can be provided in any form known from the prior art, which is appropriate for their application to the hair, including in the form of a vaporizable composition, mousse, gel, or lotion.

The composition may be in any of the conventional form including, but not limited to, shampoos, hair rinses, permanent waving compositions, waving compositions, hair dye compositions, hair straightening compositions, hair fixing products, hair styling gel products, products to use before or after a hair dye treatment, products to use before or after a permanent waving treatment, hair straightening compositions, products to use before or after a hair straightening treatment, and fixing foams.

The composition according to the invention may be vaporizable, for example by a pump, or may be a pressurized aerosol composition. It may be vaporizable by a dispensing valve controlled by a dispensing head, which in turn comprises a nozzle, which vaporizes the aerosol composition. A vaporizable composition according to the invention comprises an appropriate solvent. Advantageously, the appropriate solvent comprises at least one solvent chosen from water and lower alcohols. In accordance with the invention, the term lower alcohol means a C1–C4 aliphatic alcohol, preferably ethanol.

When the vaporizable composition according to the invention is an aerosol composition, it additionally comprises an appropriate amount of propellant. The propellant comprises compressed or liquefied gases, which are normally employed for the preparation of aerosol compositions. Suitable gasses include compressed air, carbon dioxide, nitrogen, and gases, which are soluble or otherwise in the composition, such as dimethyl ether, fluorinated or non-fluorinated hydrocarbons, and mixtures thereof.

The present invention additionally provides an aerosol device comprising a vessel comprising an aerosol composition, which comprises on the one hand a liquid phase (or juice) comprising at least one hair styling material as described above in an appropriate medium and on the other hand a propellant, and a dispenser for dispensing said aerosol composition.

The present invention additionally provides a method of treating keratinous fibers, especially hair, in which the composition according to the invention as defined above is applied to the hair before, during, or after the shaping of the hairstyle.

The compositions according to the invention can be rinsed off or not rinsed off the hair.

The present invention additionally provides the use of a composition as defined above in, or for the preparation of, a cosmetic reshapable hair styling formulation.

The composition according to the invention can be provided in any form known from the prior art, which is appropriate for their application to the hair, including in the form of a vaporizable composition, a mousse, a gel, or a lotion.

The determination of whether a polyurethane urea dispersion can provide a reshapable hair styling composition can be determined by an in vivo test. Specifically, a composition is prepared comprising the polyurethane urea dispersion and a cosmetically acceptable medium. The medium may be chosen, for example, from water, lower alcohols such as ethanol, and mixtures thereof. The composition typically comprises from about 1% to about 12% by weight active material. The compositions may be in any form noted above, including lotions.

Where the composition is in the form of a lotion, for example, the in vivo test proceeds as follows. The hair of the model is washed and then divided into two symmetrical portions, the right and the left sides. The composition is applied to one side of the head of the model, while a reference composition is applied to the other side of the head. The reference composition may, for example, be chosen from water, an existing commercial product, or another composition under study. The hairdresser dries and styles both sides of the head. The two sides of the head are separately evaluated for the styling effect, the cometic properties, and the reshapable effect. For example, once dried, the hair is brushed in different directions to remove the original styling. The hair is then brushed to either restore the original styling or to modify to form a new hair styling. The process of removing the styling, restoring/modifying the styling, and evaluating the success of restoring/modifying the styling is repeated at least one more time to determine whether the composition is a reshapable hair styling composition. A reshapable hair styling composition permits (1) the original hair styling to be restored after brushing and (2) the creation of a new hair styling after brushing, which may also be restored after brushing. If the composition to be evaluated is in another form, such as a shampoo or conditioner, the in vivo test can be appropriately modified by one skilled in the art.

It is understood that the person skilled in the art would recognize that not all formulations would provide reshapable effect for all hair types during in vivo testing and will know how to formulate and evaluate reshapable hair styling composition in view of the various hair parameters, such as length (short versus long), diameter (thin versus thick), structure (curly versus straight), condition (oily, dry, or normal); and whether the hair is colored, bleached, permed, or straightened. Thus, in vivo testing may require testing on 10–20 different individuals.

The invention may be understood more clearly with the aid of the non limiting examples which follow, and which constitutes an advantageous embodiment of the compositions in accordance with the invention.

EXAMPLES

Hair compositions according to the invention were produced with different polyurethane ureas.

1) Preparation of the Sulfonated Polyurethane Urea Dispersion

Preparation A

To prepare the sulfopolyesterpolyol, a 5 liter reaction vessel was charged with 4100 g polyethylene glycol-600 (13.67 equivalents) and 505.67 g dimethyl-5-sodiosulfoisophthalate (DMSSIP) (3.42 equivalents). The materials were dried under full vacuum at 100° C. for 1 hour. 0.08 wt % tetrabutyl titanate was subsequently added and the reaction was heated at 220° C. until approximately 85% of the theoretical methanol had been removed. The reaction temperature was reduced to 170° C. and held under vacuum for 1 hour resulting in a clear light yellow material. Calculated hydroxyl equivalent weight was 428, calculated sulfonate equivalent weight was 2632.

Preparation B

This material was prepared as preparation A above using the following materials: 1000 g polyethylene glycol-400 (5.0 equivalents), 1000 g polypropylene glycol-425 (4.7 equivalents), 359.5 g dimethyl-5-sodiosulfoisophthalate (2.43 equivalents), and 0.08 wt % tetrabutyl titanate. The product was a clear light yellow material. Calculated hydroxyl equivalent weight was 295, calculated sulfonate equivalent weight was 1879.

Preparation C

This material was prepared as preparation A above using the following materials: 3000.0 g polyethylene glycol-400 (15.0 equivalents), 555.0 g dimethyl-5-sodiosulfoisophthalate (3.75 equivalents), and 0.08 wt % tetrabutyl titanate. Drying was done at 65° C. The product was a clear light yellow material. Calculated hydroxyl equivalent weight was 305, calculated sulfonate equivalent weight was 1832.

Preparation D

This material was prepared as preparation A above using the following materials: 1404.0 g polypropylene glycol-425 (6.623 equivalents), 245.04 g dimethyl-5-sodiosulfoisophthalate (1.656 equivalents), and 0.08 wt % tetrabutyl titanate. Drying was done at 105° C. under full vacuum for 30 minutes. The reaction was heated to 245° C. followed by cooling to 145° C. then holding at 170° C. for 3 hours under full vacuum. The product was a clear yellow material. Calculated hydroxyl equivalent weight was 311, calculated sulfonate equivalent weight was 1928.

Preparation E

A 500-milliliter reaction vessel was charged with 300.0 g polyethylene glycol-300 (2.0 equivalents) and 74.0 g dimethyl-5-sodiosulfoisophthalate (0.50 equivalents). The materials were dried under full vacuum at 110° C. for 30 minutes. Nitrogen was used to release vacuum and tetrabutyl titanate (0.08 wt %) was subsequently added and the reaction was heated at 220° C. under nitrogen until approximately 85% of the theoretical methanol had been removed. The reaction temperature was reduced to 128° C. and vacuum was pulled to 0.9 mm. The reaction was heated to 170° C. held under vacuum for 1.5 hour resulting in a clear light yellow material. Calculated hydroxyl equivalent weight was 228, calculated sulfonate equivalent weight was 1432.

Preparation F

A 500-milliliter reaction vessel was charged with 225.0 g polyethylene glycol-400 (1.125 equivalents), 83.25 g dimethyl-5-sodiosulfoisophthalate (0.563 equivalents) and 1.3 g tetrabutyl titanate (0.08 wt %). The reaction was heated at 220° C. for 2 hours under nitrogen removing 15 g of methanol. The reaction temperature was reduced to 175° C. and vacuum was pulled to 1 mm. The reaction was maintained at 175° C. under vacuum for 1 hour resulting in a clear light yellow material. Calculated hydroxyl equivalent weight was 516, calculated sulfonate equivalent weight was 1032.

Example 1

To a 3 liter three neck round bottom flask, 355.0 g preparation B sulfopolyester polyol (1.145 equivalents) and 360.0 g FOMREZ™ 8056-146 (0.916 equivalents), a neopentyl glycol/1,6-hexane diol/isophthalate/adipate polyester polyol available from CK Witco, were charged and dried by heating under full vacuum. After cooling to 25° C. and repressurizing with nitrogen, 1.6 g ethanesulfonic acid (0.151 equivalents), 400.4 g isophorone diisocyanate (3.607 equivalents), and 0.02 wt % dibutyltin dilaurate were added and the reaction mixture heated to 50° C. Following a 37° C. exotherm, the reaction was maintained at approximately 75° C. for 2.5 hours.

A 12-liter reaction vessel was charged with 2088 g water and heated to 60°. The prepolymer prepared above was slowly (but continuously) added to the water over a 10–15 minute period forming a milky dispersion. The reaction was heated at 60–80° C. for two hours. This resulted in a stable dispersion having 36% solids.

Example 2

To a 2-liter, three-neck, round-bottom flask, 693.0 g preparation B sulfopolyester polyol (2.214 equivalents) and 265.5 g polypropylene glycol-1025 (0.518 equivalents) were charged and dried by heating under full vacuum. After cooling to 25° C. and repressurizing with nitrogen, 3.12 g ethanesulfonic acid (0.3 equivalents), 530.7 g isophorone diisocyanate (4.78 equivalents) and 0.02 wt % dibutyltin dilaurate were added and the reaction mixture heated to 50° C. Following a 30° C. exotherm, the reaction was maintained at approximately 75° C. for 1 hours.

A 12-liter reaction vessel was charged with 2800 g water and heated to 60° C. The prepolymer prepared above was slowly (but continuously) added to the water over a 1 hour period (keeping foaming to a minimum) forming a bluish milky dispersion. Following the addition, the reaction was heated at 75° C. for one hour. This resulted in a stable dispersion having 28.9% solids.

Example 3

To a 500 milliliter three neck round bottom flask, 45.0 g preparation C sulfopolyester polyol (0.153 equivalents), 15 g preparation D sulfopolyester polyol (0.048 equivalents), 10.0 g LEXOREZ™ 1100-220 (0.039 equivalents), a diethylene glycol/adipic acid polyester polyol available from Inolex Chemical Company, and 10.0 g FOMREZ™ 8056-146 (0.025 equivalents) were charged and dried by heating under full vacuum. After cooling to 25° C. and repressurizing with nitrogen, 0.20 g ethanesulfonic acid (0.019 equivalents), 51.56 g isophorone diisocyanate (0.465 equivalents) and 0.02 wt % dibutyltin dilaurate were added and the reaction mixture heated to 50° C. Following a 65° C. exotherm, the reaction was maintained at approximately 75° C. for 1 hour.

A 2-liter reaction vessel was charged with 310.0 g water and heated to 65° C. The prepolymer prepared above was slowly (but continuously) added to the water over a 15 minute period (keeping foaming to a minimum) forming a bluish milky dispersion. Following the addition, the reaction was heated at 75° C. for 75 minutes. This resulted in a stable dispersion having 25.7% solids.

Example 4

To a 500 milliliter three neck round bottom flask, 25.0 g preparation B sulfopolyester polyol (0.081 equivalents), 25.0 g preparation A sulfopolyester polyol (0.059 equivalents), and 20.0 g FOMREZ™ 8056-146 (0.048 equivalents) were charged and dried by heating under full vacuum. After cooling to 25° C. and repressurizing with nitrogen, 0.113 g ethanesulfonic acid (0.011 equivalents), 43.0 g DESMODUR™ W (0.328 equivalents), bis(4-isocyanato-cyclohexyl) methane available from Bayer Corporation, and 0.02 wt % dibutyltin dilaurate were added and the reaction mixture heated to 75° C. No exotherm was observed. The reaction was maintained at approximately 75° C. for 1 hour.

Another reaction vessel was charged with 265 g water and heated to 75° C. The prepolymer prepared above was slowly (but continuously) added to the water over a 10–15 minute period forming a milky dispersion. The reaction was heated at 75° C. for 75 minutes. This resulted in a stable dispersion having 22.4% solids.

Example 5

To a 500 milliliter three neck round bottom flask, 40.0 g preparation B sulfopolyester polyol (0.129 equivalents), 35.0 g preparation A sulfopolyester polyol (0.082 equivalents), 18.0 g Tone™ 0210 (0.043 equivalents), a polycaprolactone were charged and dried by heating under full vacuum. After cooling to 25° C. and repressurizing with nitrogen, 0.180 g ethanesulfonic acid (0.017 equivalents), 49.7 g isophorone diisocyanate (0.448 equivalents) and 0.02 wt % dibutyltin dilaurate were added and the reaction mixture heated to 62° C. Following a 26° C. exotherm, the reaction was maintained at approximately 75° C. for 1 hour.

Another reaction vessel was charged with 345 g water and heated to 75° C. The prepolymer prepared above was slowly (but continuously) added to the water over a 10–15 minute period forming a milky dispersion. The reaction was maintained at 75° C. for 75 minutes. This resulted in a stable dispersion having 18.4% solids.

Example 6

To a 1000 milliliter three neck round bottom flask, 95.0 g preparation B sulfopolyester polyol (0.306 equivalents), 95.0 g preparation A sulfopolyester polyol (0.224 equivalents), 40.0 g Lexorez™ 1100-220 (0.157 equivalents) and 40 g Fomrez™ 8056-146 (0.102 equivalents) were charged and dried by heating under full vacuum. After cooling to 25° C. and repressurizing with nitrogen, 0.428 g ethanesulfonic acid (0.040 equivalents), 153.19 g isophorone diisocyanate (1.380 equivalents) and 0.02 wt % dibutyltin dilaurate were added and the reaction mixture gently heated to 60° C. Following a 27° C. exotherm, the reaction was maintained at approximately 75° C. for 1 hour.

Another reaction vessel was charged with 2014 g water and heated to 75° C. The prepolymer prepared above was slowly (but continuously) added to the water over a 10-minute period forming a milky dispersion. The reaction was maintained at 75° C. for 80 minutes. This resulted in a stable dispersion having 19.1% solids.

Example 7

To a 500 milliliter three neck round bottom flask, 22.0 g preparation B sulfopolyester polyol (0.071 equivalents), 22.0 g preparation F sulfopolyester polyol (0.045 equivalents), 10.0 g Lexorez™ 1100-220 (0.039 equivalents) and 10 g Fomrez™ 8056-146 (0.025 equivalents) were charged and dried by heating under full vacuum. After cooling to 25° C. and repressurizing with nitrogen, 0.099 g ethanesulfonic acid (0.009 equivalents), 35.18 g isophorone diisocyanate (0.317 equivalents) and 0.02 wt % dibutyltin dilaurate were added and the reaction mixture was gently heated to 60° C. Following a 34° C. exotherm, the reaction was maintained at 77° C. for 1 hour.

Another reaction vessel was charged with 245 g water and heated to 75° C. The prepolymer prepared above was slowly (but continuously) added to the water over a 10-minute period forming a milky dispersion. The reaction was maintained at 75° C. for 85 minutes. This resulted in a stable dispersion having 25.4% solids.

Example 8

To a 500 milliliter three neck round bottom flask, 30.0 g preparation C sulfopolyester polyol (0.102 equivalents), 30.0 g preparation D sulfopolyester polyol (0.096 equivalents), 10.0 g Lexorez™ 1100-220 (0.039 equivalents) and 10 g Fomrez™ 8056-146 (0.025 equivalents) were charged and dried by heating under full vacuum. After cooling to 25° C. and repressurizing with nitrogen, 0.135 g ethanesulfonic acid (0.013 equivalents), 51.05 g isophorone diisocyanate (0.460 equivalents) and 0.02 wt % dibutyltin dilaurate were added and the reaction mixture was gently heated to 75° C. Following a 9.3° C. exotherm, the reaction was maintained at approximately 75° C. for 1 hour.

Another reaction vessel was charged with 306 g water and heated to 70° C. The prepolymer prepared above was slowly (but continuously) added to the water over a 10-minute period forming a bluish dispersion. The reaction was maintained at 80° C. for 75 minutes. This resulted in a stable dispersion having 35.2% solids.

Example 9

To a 500 milliliter three neck round bottom flask, 30.0 g preparation E sulfopolyester polyol (0.132 equivalents), 7.5 g Lexorez™ 1100-220 (0.029 equivalents) and 24.0 g Fomrez™ 8056-146 (0.061 equivalents) were charged and dried by heating under full vacuum. After cooling to 25° C. and repressurizing with nitrogen, 0.135 g ethanesulfonic acid (0.013 equivalents), 43.13 g isophorone diisocyanate (0.389 equivalents) and 0.02 wt % dibutyltin dilaurate were added and the reaction mixture was gently heated to 52° C. Following a 42° C. exotherm, the reaction was maintained at approximately 75° C. for 75 minutes.

Another reaction vessel was charged with 250 g water and heated to 65° C. The prepolymer prepared above was slowly (but continuously) added to the water over a 10-minute period forming a milky dispersion. The reaction was maintained at 78° C. for one hour. This resulted in a stable dispersion having 32.75% solids.

Example 10

To a 500 milliliter three neck round bottom flask, 29.76 g preparation B sulfopolyester polyol (0.096 equivalents) and 29.76 g preparation A sulfopolyester polyol (0.070 equivalents) and 23.8 g Fomrez™ 8056-146 (0.061 equivalents) were charged and dried by heating under full vacuum. After cooling to 25° C. and repressurizing with nitrogen, 0.134 g ethanesulfonic acid (0.013 equivalents), 44.0 g isophorone diisocyanate (0.397 equivalents) and 0.02 wt % dibutyltin dilaurate were added and the reaction mixture was gently heated to 50° C. Following a 53° C. exotherm, the reaction was maintained at approximately 75° C. for 1 hour.

Another reaction vessel was charged with 305 g water and heated to 70° C. The prepolymer prepared above was slowly (but continuously) added to the water over a 15-minute period forming a milky dispersion. The reaction was maintained at 75° C. for one hour. This formed a stable dispersion having 27.4% solids.

Example 11

To a 500 milliliter three neck round bottom flask, 25.0 g preparation B sulfopolyester polyol (0.081 equivalents), 25.0 g preparation A sulfopolyester polyol (0.059 equivalents) and 20 g Fomrez™ 8056-146 (0.051 equivalents) were charged and dried by heating under full vacuum. After cooling to 25° C. and repressurizing with nitrogen, 0.113 g ethanesulfonic acid (0.011 equivalents), 43.6 g Desmodur™ W (0.333 equivalents) and 0.02 wt % dibutyltin dilaurate were added and the reaction mixture was gently heated to 50° C. Following a 68.6° C. exotherm, the reaction was maintained at approximately 75° C. for 1 hour.

Another reaction vessel was charged with 280 g water and heated to 65° C. The prepolymer prepared above was slowly (but continuously) added to the water over a 10-minute period resulting in an almost clear dispersion. The reaction was heated at 82° C. for one hour. The resulting dispersion had 23.65% solids.

Example 12

To a 500 milliliter three neck round bottom flask, 20.0 g preparation D sulfopolyester polyol (0.064 equivalents) and 55.0 g preparation C sulfopolyester polyol (0.186 equivalents), 18.0 g Tone™ 0210 (0.043 equivalents) and 5.0 g polyethylene glycol-3400 (0.003 equivalents) were charged and dried by heating under full vacuum. After cooling to 25° C. and repressurizing with nitrogen, 0.090 g ethanesulfonic acid (0.009 equivalents), 57.7 g isophorone diisocyanate (0.520 equivalents) and 0.02 wt % dibutyltin dilaurate were added and the reaction mixture was gently heated to 50° C. To Following a 70° C. exotherm, the reaction was maintained at approximately 75° C. for 1 hour.

Another reaction vessel was charged with 380 g water and heated to 65° C. The prepolymer prepared above was slowly (but continuously) added to the water over a 10-minute period forming a milky dispersion. The reaction was maintained at 75° C. for three hours. The resulting stable dispersion had 22.5% solids.

Example 13

To a 1 liter three neck round bottom flask, 168.3 g preparation B sulfopolyester polyol (0.538 equivalents) and 82.0 g polypropylene glycol-1025 (0.160 equivalents) were charged and dried by heating under full vacuum. After cooling to 25° C. and repressurizing with nitrogen, 0.757 g ethanesulfonic acid (0.072 equivalents), 135.52 g isophorone diisocyanate (1.221 equivalents) and 0.02 wt % dibutyltin dilaurate were added and the reaction mixture was subsequently heated to 50° C. Following a 25° C. exotherm, the reaction was maintained at approximately 75° C. for 90 minutes. The reaction was shut down overnight then reheated to 80° C. the next day. Following a 32° C. exotherm, the reaction was maintained at approximately 75° C. for 1 hour.

A reaction vessel was charged with 137.68 g water and 2.8 g ethylene diamine (0.0933 equivalents) and heated to 50° C. Prewarmed prepolymer prepared above (71.8 g) was slowly (but continuously) added to the aqueous amine solution over a 10-minute period forming a bluish then milky dispersion. Following the addition, the reaction was heated at 70° C. for 30 minutes. The resulting stable dispersion had 26.0% solids.

Example 14

To a 1 liter three neck round bottom flask, 168.3 g preparation B sulfopolyester polyol (0.538 equivalents) and 82.0 g polypropylene glycol-1025 (0.160 equivalents) were charged and dried by heating under full vacuum. After cooling to 25° C. and repressurizing with nitrogen, 0.757 g ethanesulfonic acid (0.072 equivalents), 135.52 g isophorone diisocyanate (1.221 equivalents) and 0.02 wt % dibutyltin dilaurate were added and the reaction mixture was subsequently heated to 50° C. Following a 25° C. exotherm, the reaction was maintained at approximately 75° C. for 90 minutes. The reaction was shut down overnight then reheated to 80° C. the next day. Following a 32° C. exotherm, the reaction was maintained at approximately 75° C. for 1 hour.

A reaction vessel was charged with 193.8 g water and 7.4 g Dytek™ A (0.128 equivalents), a 5-methyl-1,5-pentanediamine, and heated to 50° C. 99.21 g prewarmed prepolymer prepared above was slowly added to the aqueous amine solution over a 10-minute period forming a bluish then milky dispersion. Following the addition, the reaction was heated at 70° C. for 30 minutes. The resulting stable dispersion had 29.0% solids.

Example 15

A 50/50 mixture of the dispersion from Example 3 and a dispersion comprising AQ 1350 by the Eastman Chemical Co. as disclosed in WO 98/38969 was made.

Example 16

A 25/75 mixture of the dispersion from Example 1 and a dispersion comprising AQ 1350 by the Eastman Chemical Co. as disclosed in WO 98/38969 was made.

Example 17

A 25/75 mixture of the dispersion from Example 1 and the dispersion from Example 2 can be made.

2) Preparation of the Hair Styling Compositions

Four hair styling compositions in accordance with the invention were prepared using the components and amounts in weight percent listed hereafter. The testing was conducted on several models with one part of the head receiving one of the two reference compositions and the other side of the head receiving the tested composition. The compositions were applied to wet hair after shampooing. The hair was then dried, brushed, and evaluated.

Reference 1:

| | |
|---|---|
| AQ 1350 | 4% active material |
| Ethanol | 20% |
| Water | qsp 100% |

Reference 2:

| | |
|---|---|
| Water | 100% |

Formulation A:

| | |
|---|---|
| Example 1 | 4% active material |
| Water | qsp 100% |

Formulation A imparted good hairstyling and a reshapable effect better than reference 2 with good cosmetic properties.

Formulation B:

| | |
|---|---|
| Example 2 | 4% active material |
| Water | qsp 100% |

Formulation B imparted good hairstyling and a reshapable effect but not as good as reference 1 with adequate cosmetic properties.

Formulation C:

| | |
|---|---|
| Example 3 | 4% active material |
| Water | qsp 100% |

Formulation C imparted good hairstyling and a reshapable effect better than reference 2 with good cosmetic properties.

What is claimed is:

1. A reshapable hair styling composition comprising, in a cosmetic vehicle appropriate for hair, at least one polyurethane urea comprising the residue of at least one sulfonated polyol, wherein said composition provides a reshapable effect.

2. A reshapable hair styling composition comprising, in a cosmetic vehicle appropriate for hair, at least one dispersion comprising at least one sulfonated polyurethane urea obtained by reacting:
   (a) at least one sulfonated polyol;
   (b) at least one non-sulfonated polyol;
   (c) at least one polyisocyanate chosen from aliphatic polyisocyanates, having 1 to 25 carbon atoms, and cycloaliphatic polyisocyanates, having 3 to 25 carbon atoms; and
   (d) excess water, wherein:
      the sulfonated polyurethane urea has been chain-extended and wherein said composition provides a reshapable effect.

3. The composition according to claim 2, wherein said at least one sulfonated polyurethane urea has been chain-extended with water.

4. The composition according to claim 3, wherein the reaction product of (a), (b), and (c) has an isocyanate to hydroxyl ratio ranging from about 1.3:1 to about 2.5:1.

5. The composition according to claim 4, wherein the reaction product of (a), (b), and (c) with (d) has a sulfonate equivalent weight of from about 1000 to about 8500 and comprises a polyurea segment of the following formula:

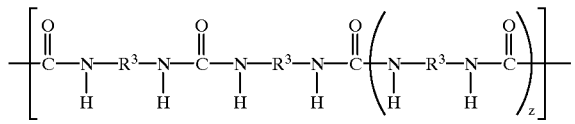

wherein z is an integer from 0 to 6; and $R^3$ is chosen from aliphatic groups, having 1 to 25 carbon atoms, and cycloaliphatic groups, having 3 to 25 carbon atoms, derived from said aliphatic and cycloaliphatic polyisocyanate.

6. The composition according to claim 2, wherein said at least one dispersion is a colloidal dispersion.

7. The composition according to claim 4, wherein said reaction product of (a), (b), and (c) has an isocyanate to hydroxyl ratio of about 1.65:1 to about 1.85:1.

8. The composition according to claim 5, wherein said reaction product of (a), (b), and (c) with (d) has a sulfonate equivalent weight of from about 3000 to about 6000.

9. The composition according to claim 2, further comprising at least one additional polymer.

10. The composition according to claim 9, wherein said at least one additional polymer is chosen from anionic, cationic, amphoteric, nonionic, and zwitterionic polymers.

11. The composition according to claim 2, wherein said at least one sulfonated polyol is obtained by reacting:
   (a) a compound chosen from dimethyl-5-sodiosulfoisophthalate and 5-sodiosulfoisophthalic acid and
   (b) at least one polyol.

12. The composition according to claim 11, wherein said at least one polyol is chosen from polyether polyols, polyester polyols, and polycaprolactone polyols.

13. The composition according to claim 12, wherein said at least one polyol is chosen from polyethylene glycol-600, polyethylene glycol-400, polypropylene glycol-425, polyethylene glycol-300, and polyethylene glycol-200.

14. The composition according to claim 2, wherein said at least one non-sulfonated polyol is chosen from polyether polyols, polyester polyols, and polycaprolactone polyols.

15. The composition according to claim 14, wherein said at least one non-sulfonated polyol is chosen from diethylene glycol/adipic acid polyester polyols, neopentyl glycol/1,6-hexanediol/isophthalate/adipate polyester polyols, polyethylene glycols, polycaprolactone diols, and polypropylene glycols.

16. The composition according to claim 2, wherein said at least one polyisocyanate is a diisocyanate.

17. The composition according to claim 16, wherein said diisocyanate is chosen from isophorone diisocyanates, bis(4-isocyanatocyclohexyl)methanes, trimethyl-1,6-diisocyanato hexanes, and mixtures thereof.

18. The composition according to claim 2, wherein said at least one sulfonated polyurethane urea has a Tg ranging from about −100 to about 15° C.

19. The composition according to claim 2, further comprising at least one other constituent, which is conventional in cosmetics, chosen from preservatives, perfumes, UV filters, active haircare agents, plasticizers, anionic, cationic, amphoteric, nonionic, and zwitterionic surfactants, hair conditioning agents such as silicone fluids, fatty esters, fatty alcohol, long chain hydrocarbons, emollients, lubricants, and penetrants such as lanolin compounds, protein hydrolysates, and other protein derivatives, dyes, tints, bleaches, reducing agents, pH adjusting agents, sunscreens, preservatives, thickening agents, and perfumes.

20. An aerosol device comprising a vessel, which comprises (1) an aerosol composition, which comprises a liquid phase comprising at least one composition comprising at least one dispersion comprising at least one sulfonated polyurethane urea obtained by reacting:
   (a) at least one sulfonated polyol;
   (b) at least one non-sulfonated polyol;
   (c) at least one polyisocyanate chosen from aliphatic polyisocyanates, having 1 to 25 carbon atoms, and cycloaliphatic polyisocyanates, having 3 to 25 carbon atoms; and
   (d) excess water, wherein:
      the sulfonated polyurethane urea has been chain-extended and wherein said composition provides a reshapable effect; and a propellant, and (2) a dispenser.

21. (Amended) The aerosol device according to claim 20, wherein said at least one sulfonated polyurethane urea has been chain-extended with water.

22. The aerosol device according to claim 21, wherein the reaction product of (a), (b), and (c) has an isocyanate to hydroxyl ratio ranging from about 1.3:1 to about 2.5:1.

23. The aerosol device according to claim 22, wherein the

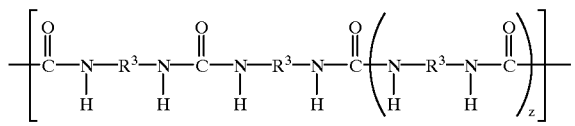

reaction product of (a), (b), and (c) with (d) has a sulfonate equivalent weight of from about 1000 to about 8500 and comprises a polyurea segment of the following formula:
wherein z is an integer from 0 to 6; and $R^3$ is chosen from aliphatic groups, having 1 to 25 carbon atoms, and cycloaliphatic groups, having 3 to 25 carbon atoms, derived from said aliphatic and cycloaliphatic polyisocyanate.

24. A method of cosmetically treating hair, comprising the application of a composition comprising at least one dispersion comprising at least one sulfonated polyurethane urea obtained by reacting:
(a) at least one sulfonated polyol;
(b) at least one non-sulfonated polyol;
(c) at least one polyisocyanate chosen from aliphatic polyisocyanates, having 1 to 25 carbon atoms, and cycloaliphatic polyisocyanates, having 3 to 25 carbon atoms; and
(d) excess water, wherein:
the sulfonated polyurethane urea has been chain-extended and wherein said composition provides a reshapable effect;
to the hair before, during, or after the shaping of the hairstyle.

25. The method of cosmetically treating hair according to claim 24, wherein said at least one sulfonated polyurethane urea has been chain-extended with water.

26. The method of cosmetically treating hair according to claim 25, wherein the reaction product of (a), (b), and (c) has an isocyanate to hydroxyl ratio ranging from about 1.3:1 to about 2.5:1.

27. The method of cosmetically treating hair according to claim 26, wherein the reaction product of (a), (b), and (c) with (d) has a sulfonate equivalent weight of from about 1000 to about 8500 and comprises a polyurea segment of the following formula:

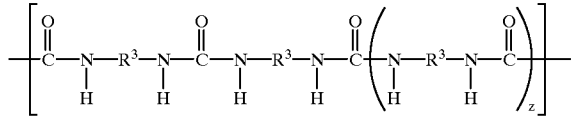

wherein z is an integer from 0 to 6; and $R^3$ is chosen from aliphatic groups, having 1 to 25 carbon atoms, and cycloaliphatic groups, having 3 to 25 carbon atoms, derived from said aliphatic and cycloaliphatic polyisocyanate.

28. A method of manufacturing a reshapable hair styling composition comprising the inclusion of at least one dispersion comprising at least one sulfonated polyurethane urea obtained by reacting:
(a) at least one sulfonated polyol;
(b) at least one non-sulfonated polyol;
(c) at least one polyisocyanate chosen from aliphatic polyisocyanates, having 1 to 25 carbon atoms, and cycloaliphatic polyisocyanates, having 3 to 25 carbon atoms; and
(d) excess water.

29. The method of manufacturing a reshapable hairstyling composition according to claim 28, wherein said at least one sulfonated polyurethane urea has been chain-extended with water.

30. The method of manufacturing a reshapable hairstyling composition according to claim 29, wherein the reaction product of (a), (b), and (c) has an isocyanate to hydroxyl ratio ranging from about 1.3:1 to about 2.5:1.

31. The method of manufacturing a reshapable hairstyling composition according to claim 30, wherein the reaction product of (a), (b), and (c) with (d) has a sulfonate equivalent weight of from about 1000 to about 8500 and comprises a polyurea segment of the following formula:

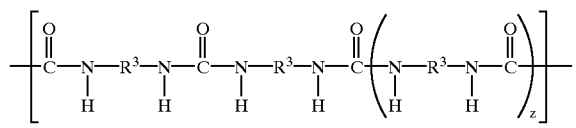

wherein z is an integer from 0 to 6; and $R^3$ is chosen from aliphatic groups, having 1 to 25 carbon atoms, and cycloaliphatic groups, having 3 to 25 carbon atoms, derived from said aliphatic and cycloaliphatic polyisocyanate.
wherein:
the sulfonated polyurethane urea has been chain-extended and wherein said composition provides a reshapable effect.

32. An aerosol device comprising a vessel, which comprises (1) an aerosol composition, which comprises a liquid phase comprising at least one polyurethane urea comprising the residue of at least one sulfonated polyol, wherein said composition provides a reshapable effect, and a propellant, and (2) a dispenser.

33. A method of cosmetically treating hair, comprising the application of a composition comprising at least one polyurethane urea comprising the residue of at least one sulfonated polyol to the hair before, during, or after the shaping of the hairstyle, wherein said composition provides a reshapable effect.

34. A method of manufacturing a reshapable hair styling composition comprising the inclusion of at least one polyurethane urea comprising the residue of at least one sulfonated polyol, wherein said composition provides a reshapable effect.

35. A reshapable hair styling composition comprising, in a cosmetic vehicle appropriate for hair, at least one dispersion comprising at least one polyurethane urea comprising the residue of at least one sulfonated polyol, wherein said composition provides a reshapable effect.

36. A reshapable hair styling composition comprising, in a cosmetic vehicle appropriate for hair, at least one colloidal dispersion comprising at least one polyurethane urea comprising the residue of at least one sulfonated polyol, wherein said composition provides a reshapable effect.

* * * * *

UNITED STATES PATENT AND TRADEMARK OFFICE
CERTIFICATE OF CORRECTION

PATENT NO. : 6,517,821 B1
DATED : February 11, 2003
INVENTOR(S) : Isabelle Rollat et al.

It is certified that error appears in the above-identified patent and that said Letters Patent is hereby corrected as shown below:

Column 20,
Line 5, "(d) excess water." should read -- (d) excess water,
wherein:
    the sulfonated polyurethane urea has been chain-extended and wherein said composition provides a reshapable effect. --.
Line 30, after "polyisocyanate.", delete
"wherein:
    the sulfonated polyurethane urea has been chain-extended and wherein said composition provides a reshapable effect.".

Signed and Sealed this

Seventeenth Day of June, 2003

JAMES E. ROGAN
*Director of the United States Patent and Trademark Office*